(12) United States Patent
Mori et al.

(10) Patent No.: US 8,277,625 B2
(45) Date of Patent: Oct. 2, 2012

(54) GAS SENSING DEVICE AND GAS SENSOR

(75) Inventors: Shigeki Mori, Komaki Aichi (JP);
Masaki Mizutani, Komaki Aichi (JP);
Nobuo Furuta, Kasugai Aichi (JP);
Yuuya Nakayama, Kasugai Aichi (JP)

(73) Assignee: NGK Spark Plug Co., Ltd. (JP)

( * ) Notice: Subject to any disclaimer, the term of this patent is extended or adjusted under 35 U.S.C. 154(b) by 1029 days.

(21) Appl. No.: 11/580,661

(22) Filed: Oct. 13, 2006

(65) Prior Publication Data

US 2007/0084724 A1    Apr. 19, 2007

(30) Foreign Application Priority Data

Oct. 17, 2005  (JP) ................................. 2005-301168
Aug. 21, 2006  (JP) ................................. 2006-223729

(51) Int. Cl.
*G01N 27/407* (2006.01)
*G01N 27/41* (2006.01)

(52) U.S. Cl. .................... 204/429; 204/424; 204/426

(58) Field of Classification Search .................. 204/400, 204/421–435; 205/781, 783.5, 784.5
See application file for complete search history.

(56) References Cited

U.S. PATENT DOCUMENTS

| | | | | |
|---|---|---|---|---|
| 4,859,307 A * | 8/1989 | Nishizawa et al. | ............ | 204/425 |
| 5,419,828 A * | 5/1995 | Nakano et al. | ................ | 204/425 |
| 6,205,843 B1 | 3/2001 | Tanaka et al. | ................ | 73/31.06 |
| 6,533,921 B2 * | 3/2003 | Miyata et al. | ................. | 205/781 |
| 2003/0106795 A1 | 6/2003 | Katafuchi et al. | ............ | 204/424 |
| 2004/0154920 A1 * | 8/2004 | Schneider et al. | ............ | 204/431 |
| 2004/0217002 A1 * | 11/2004 | Naito et al. | ................... | 204/424 |

FOREIGN PATENT DOCUMENTS

| | | |
|---|---|---|
| EP | 0 857 966 A2 | 8/1998 |
| EP | 0857966 A2 * | 12/1998 |
| EP | 1 464 954 A2 | 10/2004 |
| JP | 10-221287 | 8/1998 |
| JP | 10-221304 | 8/1998 |
| JP | 2002-333422 | 11/2002 |
| JP | 2003-247969 | 9/2003 |
| JP | 2003-294687 | 10/2003 |

OTHER PUBLICATIONS

European Search Report (from corresponding European App. No. 06021718.9)—6 pages.

* cited by examiner

*Primary Examiner* — Kaj K Olsen
*Assistant Examiner* — Kourtney R Carlson
(74) *Attorney, Agent, or Firm* — Kusner & Jaffe

(57) ABSTRACT

This invention provides a gas sensing device and gas sensor including a porous portion in which a first porous portion absorbs phosphorus and silicone sufficiently so as to suppress generation of clogging in a second porous portion meeting demands for intensifying the performance and accuracy of a gas sensor, so that the accuracy of detection of air-fuel ratio is further improved.

7 Claims, 6 Drawing Sheets

GAS SENSING DEVICE AND GAS SENSOR

FIELD OF THE INVENTION

The present invention relates to a gas sensing device and gas sensor for use for combustion control or the like of an internal combustion engine and a manufacturing method thereof. More particularly, the present invention relates to a gas sensing device and gas sensor capable of preventing the detection accuracy of air-fuel ratio from dropping due to poisoning.

BACKGROUND OF THE INVENTION

As a gas sensor which is installed in the exhaust system of an internal combustion engine and used for combustion control of the internal combustion engine by detecting the concentration of oxygen in exhaust gas, conventionally, an oxygen sensor has been well known. This oxygen sensor, for example, comprises a cylindrical main body metal and a sheet-like gas sensing device held by the main body metal. The gas sensing device comprises a first solid electrolyte layer extending in the length direction, a cell having a first opposing electrode formed on front and rear surfaces on the side of the front end exposed to measuring object gas of the first solid electrolyte layer and a first porous portion overlaid on the cell. One of the opposing electrodes of the cell is disposed in a measuring chamber to which measuring object gas is to be introduced. The first porous portion is provided to control the diffusion rate of the measuring object gas introduced into the measuring chamber.

Some types of fuel and engine oil used in the internal combustion engine of an automobile or the like contain phosphorous or silicone. When this fuel or engine oil is used, phosphorous or silicone adheres to the surface of the first porous portion so as to close pores in the porous portion so that the first porous portion is clogged. As a result, the diffusion resistance of the first porous portion changes, so that the detection accuracy of the air-fuel ratio of the gas sensor can drop.

To meet generation of clogging in the porous portion and abnormality in the electrode, providing of a second porous portion for preventing poisoning by phosphorus or silicone between the first porous portion and outside has been known. See, for example, Japanese Paten Application Laid-Open No. 10-221304 to Tsuzuki et al. and U.S. Pat. No. 5,925,814 to Tsuzuki et al. Generation of clogging in the first porous portion can be suppressed by sucking phosphorous or silicone with the second porous portion. Thus, changes in diffusion resistance in the first porous portion can be suppressed to block drop of the detection accuracy of the air-fuel ratio of the gas sensor.

However, in recent years, higher performance and intensified accuracy of the gas sensor have been demanded and thus, suppressing of clogging generated in the first porous portion by sucking more phosphorous and silicone by means of the second porous portion has been considered important. However, there is a fear that the second porous portion described in the aforementioned patent documents cannot suck phosphorus and silicone sufficiently enough for higher performance and intensified accuracy of the gas sensor. More specifically, the second porous portion of the aforementioned patent documents is so constructed that all measuring object gas is introduced into an introduction passage in order to introduce to a measuring chamber and an interface between the introduction passage and the second porous portion is exposed on an external face of the gas sensing device. In case of such a gas sensing device, when the measuring object gas is introduced into the second porous portion, part of phosphorous and silicone invades into the first porous portion from outside using this interface as a passage without being sucked by the second porous portion. As a result, suppression of clogging generated in the first porous portion is not achieved sufficiently, so that there is a fear that the first porous portion cannot be applied to intensification of performance and accuracy of the gas sensor.

SUMMARY OF THE INVENTION

The present invention has been accomplished in views of the conventional problems and an advantage of the invention is a gas sensing device and gas sensor in which phosphorous and silicone can be sucked by the second porous portion thereof securely so as to suppress generation of clogging in the first porous portion thereby meeting a demand for intensifying performance and accuracy of the gas sensor, the gas sensing device being capable of improving the accuracy of detection on air-fuel ratio.

To achieve the above-described advantage, according to an aspect of the present invention, there is provided a sheet-like gas sensing device comprising a first cell having a first solid electrolyte layer and first opposing electrodes formed on the front and rear faces of the first solid electrolyte layer and a hollow measuring chamber to which gas is introduced through a first porous portion and one of the first opposing electrode faces, wherein at least part of an external face directed to the outermost virtual face connecting outermost faces of the gas sensing device of the first porous portion is located inside the outermost virtual face so that the part is dented from the outermost virtual face, forming a concave portion including the external face, the sheet-like gas sensing device further comprising a second porous portion having a smaller diffusion resistance than the first porous portion with part thereof invading into the concave portion while being in contact with at least an opening edge of the concave portion.

By disposing the second porous portion at least in contact with the opening edge of the concave portion, an interface (opening edge of the concave portion in the present invention, between an introduction passage and the second porous portion can be prevented from being exposed to the outermost virtual face of the gas sensing device thereby blocking gas from invading into the first porous portion from outside through this interface. Thus, generation of clogging in the first porous portion can be suppressed to improve the accuracy of detection of air-fuel ratio by changes in diffusion resistance of a measuring object gas.

Further, part of this second porous portion invades into the concave portion. Because part of the second porous portion invades into the concave portion so as to form a wedge-like configuration, the second porous portion can be prevented from being separated from the gas sensing device as compared to a case where the second porous portion is disposed in contact with only the opening edge of the concave portion of the gas sensing device.

To allow the second porous portion to absorb more phosphorous and silicone, the thickness of the second porous portion needs to be intensified. However, as the thickness of the second porous portion is intensified, the second porous portion is enlarged, thereby leading to tremendous enlargement of the gas sensing device. Usually, when the gas sensing device is heated by a heater so that it is activated, it can detect air-fuel ratio. However, if the gas sensing device is enlarged tremendously, it takes more time for the gas sensing device to be activated (hereinafter, referred to as activation time). As a consequence, there is a fear that the gas sensing device cannot detect air-fuel ratio early. Contrary to this, by introducing part of the second porous portion into the concave portion of the gas sensing device, the thickness of the second porous portion can be secured without enlarging the gas sensing device tremendously, and as a consequence, the second porous portion can absorb more phosphorus and silicone without delaying the activation time of the gas sensing device.

In the meantime, the diffusion resistance of the second porous portion is set smaller than the diffusion resistance of the first porous portion. This prevents the measuring object gas from being suppressed in diffusion rate by the second porous portion for absorbing phosphorous and silicone thereby blocking the accuracy of detection of air-fuel ratio from dropping.

The second porous portion may be dented into the concave portion while in contact with only the opening edge of the concave portion or may be dented into the concave portion while covering the entire periphery of the outermost virtual face of the gas sensing device. That is, the second porous portion only need to make contact with the opening edge such that the opening edge of the concave portion is not exposed outside. Further, the outermost virtual face connecting the outermost faces of the gas sensing device mentioned in the present invention refers to a virtual face produced by connecting respective faces located at the outermost side of the sheet-like gas sensor and if speaking in detail, corresponds to a virtual face shown in FIGS. 4, 6, 7 described in embodiments below.

According to another aspect of the present invention, there is provided the gas sensing device wherein a second cell having a second solid electrolyte layer and second opposing electrodes formed on the front and rear faces of the second solid electrolyte layer is overlaid on the first cell through the first porous portion with one of the second opposing electrodes facing the measuring chamber, the gas sensing device further comprising an insulating layer formed between the first cell and the second cell, which forms the measuring chamber with the first cell, the second cell and the first porous portion.

By adopting the above-described structure for the gas sensing device, a gas sensing device in which the second porous portion is in contact with the opening edge of the concave portion while part thereof invades into the concave portion can be achieved. Consequently, generation of clogging in the first porous portion can be suppressed so as to improve the accuracy of detection of air-fuel ratio by changes in diffusion resistance of the measuring object gas thereby preventing the second porous portion from being separated.

In the gas sensing device of the present invention, preferably, the minimum thickness of the second porous portion provided in the concave portion from an external face thereof to an internal face directed to the first porous portion is 130 µm or more.

By setting the minimum thickness between the external face of the second porous portion provided in the concave portion and the internal face to more than 130 µm, a distance over which the measuring object gas passes through the second porous portion can be increased, so that more phosphorous and silicone can be absorbed by the second porous portion. Consequently, generation of clogging in the first porous portion can be suppressed so as to improve the accuracy of detection of air-fuel ratio by changes in diffusion resistance of the measuring object gas. If the minimum distance of the second porous portion is less than 130 µm, sometimes, the above-described effect cannot be obtained. Although the distance of the second porous portion is preferred to be as long as possible, preferably the maximum thickness between the external face of the second porous portion provided in the concave portion and the internal face is 300 µm or less if considering the activation time of the gas sensing device. In the meantime, the minimum thickness from the external face of the second porous portion provided in the concave portion and the internal face directed to the first porous portion refers to a distance of straight line of an area containing the second porous portion located in the concave portion of the second porous portion.

Exhaust gas passing through the exhaust pipe of an internal combustion engine contains water droplet or oil droplet and if the water droplet or the like adheres to the gas sensing device when the gas sensor is used, crack may occur in the gas sensing device. If speaking in detail, because the gas sensing device is exposed to exhaust gas (measuring object gas) and heated by a heater when the gas sensor is used, when water droplet or the like makes contact therewith, a large difference in temperature occurs between the portion which the water droplet adheres to and its surrounding, thereby resulting in generation of crack due to thermal shock. As for the portion in which crack occurs due to contact of water droplet, if water droplet adheres to the corner portion extending in the length direction of the gas sensing device, thermal shock is likely to concentrate on that corner portion thereby often causing a crack.

In the gas sensing device of the present invention, preferably, the second porous portion covers the corner portion in the length direction of the gas sensing device and the thickness of the second porous portion from the corner portion is 20 µm or more. By covering the corner portion in the length direction of the gas sensing device with porous substance based on the fact that the second porous portion is composed of the porous substance, water droplets adhering to the second porous portion penetrate slowly while being diffused into a number of pores, so that the water droplets can be diffused before they reach the corner portion of the gas sensing device. As a consequence, thermal shock generated in the corner portion of the gas sensing device can be suppressed thereby suppressing generation of crack in the gas sensing device.

Preferably, the thickness of the second porous portion from the outermost virtual face of the gas sensing device is 30 µm or more in order to prevent generation of crack due to wetting and more preferably, 50 µm or more. On the other hand, preferably, the thickness of the second porous portion is 300 µm or less considering the activation time of the gas sensing device.

In the meantime, the corner portion extending in the length direction mentioned in the present invention refers to a part connecting any one of front and rear faces extending in the length direction with any one of both side faces, of the external faces of the sheet-like gas sensing device. Then, the corner portion is not restricted to the top of a line in which two faces intersect (that is, ridge line) but includes a curved portion which connects two faces with for example, a round configuration. The second porous portion may be formed to cover one or more corner portions. That is, the second porous portion may be formed by selecting one or more of the corner portions likely to be wet considering the installation positions within the gas sensor. The second porous portion may be so constructed to cover not only the first porous portion and corner portion but also the external face of the gas sensing device. A sentence "the thickness of the second porous portion from the corner portion is 20 µm or more" in the present invention means that in a section in the thickness direction of the gas sensing device, a virtual circle having a diameter of 20 µm is formed (included) between the corner portion of the gas sensing device and the surface of the second porous portion.

In the gas sensing device of the present invention, preferably, the BET specific surface area of the second porous portion is 1.0 m$^2$/g or more. If the BET specific surface area of the second porous portion is set to 1.0 m$^2$/g or more, the diameter of particles which form the second porous portion becomes smaller, so that the second porous portion can absorb more phosphorous and silicone. Thus, generation of clogging in the first porous portion can be further suppressed to improve the accuracy of detection of air-fuel ratio by changes in diffusion resistance of a measuring object gas. If the BET specific surface area of the second porous portion is less than 1.0 m$^2$/g, it is difficult to obtain the above-described effect. In the meantime, the BET specific surface area can be measured according to the BET method.

In the gas sensing device of the present invention, the first porous portion is overlaid on the first cell and the measuring chamber is defined by the first cell and the first porous portion and further, the shielding layer is provided to be overlaid on the first cell via the first porous portion.

By adopting the above-described structure for the gas sensing device, a gas sensing device in which the second porous portion is in contact with the opening edge of the concave portion while part thereof invades into the concave portion can be achieved. Consequently, generation of clogging in the first porous portion can be suppressed so as to improve the accuracy of detection of air-fuel ratio by changes in diffusion resistance of the measuring object gas thereby preventing the second porous portion from being separated.

In the gas sensing device having the above-described structure, the concave portion may be formed at, at least one portion of four portions, both side faces of the gas sensing device, front end face and rear end face and the second porous portion needs to be dented into the concave portion. Further, the concave portion may be formed at all four portions, both side faces of the gas sensing device, front end face and rear end face and the second porous portion may be dented into the concave portion.

In the gas sensing device of the present invention, preferably, the minimum thickness of the second porous portion formed outside the first porous portion is 130 μm or more in a direction perpendicular to the laminating direction.

By setting the minimum thickness of the second porous portion formed outside the first porous portion to more than 130 μm, a distance over which the measuring object gas passes through the second porous portion can be increased, so that more phosphorous and silicone can be absorbed by the second porous portion. Consequently, generation of clogging in the first porous portion can be further suppressed so as to improve the accuracy of detection of air-fuel ratio by changes in diffusion resistance of the measuring object gas. If the minimum distance of the second porous portion is less than 130 μm, sometimes, the above-described effect cannot be obtained. Although the distance of the second porous portion is preferred to be as long as possible, preferably the maximum thickness of the second porous portion formed outside the first porous portion is 300 μm or less if considering the activation time of the gas sensing device.

Exhaust gas passing through the exhaust pipe of an internal combustion engine contains water droplet or oil droplet and if the water droplet or the like adheres to the gas sensing device when the gas sensor is used, crack can occur in the gas sensing device. If speaking in detail, because the gas sensing device is exposed to exhaust gas (measuring object gas) and heated by a heater when the gas sensor is used, when water droplet or the like makes contact therewith, a large difference in temperature occurs between the portion which the water droplet adheres to and its surrounding, thereby resulting in generation of crack due to thermal shock. As for the portion in which crack occurs due to contact of water droplet, if water droplet adheres to the corner portion extending in the length direction of the gas sensing device, thermal shock is likely to concentrate on that corner portion thereby often causing a crack.

In the gas sensing device of the present invention, preferably, the second porous portion covers the corner portion in the length direction of the gas sensing device and the thickness of the second porous portion from the corner portion is 20 μm or more. By covering the corner portion in the length direction of the gas sensing device with porous substance based on the fact that the second porous portion is composed of the porous substance, water droplets adhering to the second porous portion penetrate slowly while being diffused into a number of pores, so that the water droplets can be diffused before they reach the corner portion of the gas sensing device. As a consequence, thermal shock generated in the corner portion of the gas sensing device can be suppressed thereby suppressing generation of crack in the gas sensing device.

Preferably, the thickness of the second porous portion from the outermost virtual face of the gas sensing device is 30 μm or more in order to prevent generation of crack due to wetting and more preferably, 50 μm or more. On the other hand, preferably, the thickness of the second porous portion is 300 μm or less considering the activation time of the gas sensing device.

In the meantime, the corner portion extending in the length direction mentioned in the present invention refers to a part connecting any one of front and rear faces extending in the length direction with any one of both side faces, of the external faces of the sheet-like gas sensing device. Then, the corner portion is not restricted to the top of a line in which two faces intersect (that is, ridge line) but includes a curved portion which connects two faces with for example, a round configuration. The second porous portion may be formed to cover one or more corner portions. That is, the second porous portion may be formed by selecting one or more of the corner portions likely to be wet considering the installation positions within the gas sensor. The second porous portion may be so constructed to cover not only the first porous portion and corner portion but also the external face of the gas sensing device. A sentence "the thickness of the second porous portion from the corner portion is 20 μm or more" in the present invention means that in a section in the thickness direction of the gas sensing device, a virtual circle having a diameter of 20 μm is formed (included) between the corner portion of the gas sensing device and the surface of the second porous portion.

The gas sensor of the present invention is a gas sensor comprising: a cylindrical main body metal and a gas sensing device held by the main body metal, wherein the gas sensing device is a gas sensing device according to the aspect of the present invention.

By using the above-described gas sensing device for the gas sensor of the present invention, it can detect air-fuel ratio at an excellent accuracy by changes in diffusion resistance of the measuring object gas.

DETAILED DESCRIPTION OF PREFERRED EMBODIMENTS

Hereinafter, a gas sensor according to the first embodiment of the present invention will be described with reference to the accompanying drawings. In the first embodiment, a total area liner air-fuel ration sensor 2 including a gas sensing device for detecting specific gas in exhaust gas as a measuring object gas for use in air-fuel ratio feedback control in an internal combustion engine of an automobile and the like, this total area liner air-fuel ration sensor being mounted in an exhaust pipe of the internal combustion engine, will be described.

Figure 1:
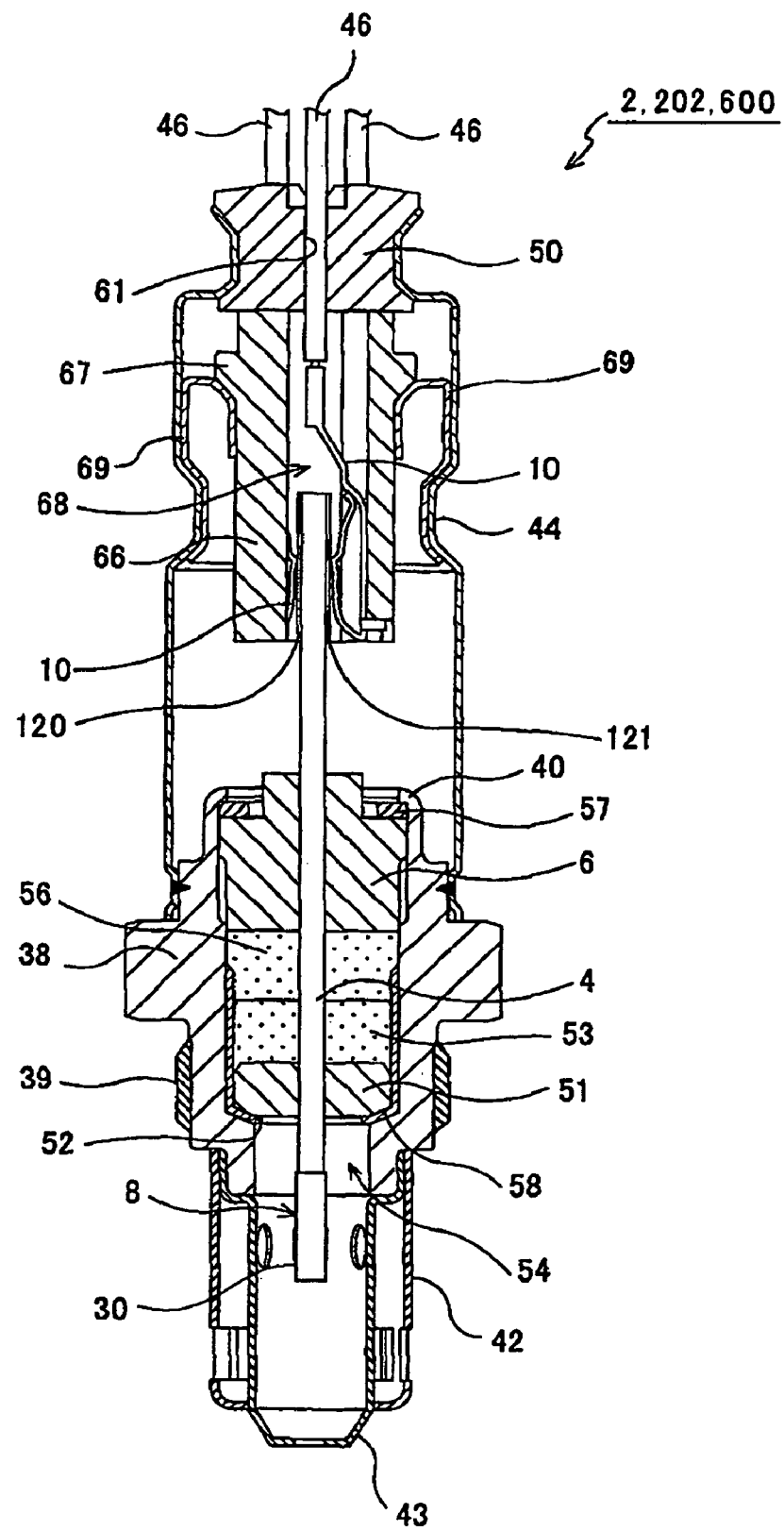
FIG. 1 is a sectional view of a gas sensor 2 of the first embodiment.

FIG. 1 is a sectional view showing the entire structure of the liner air-fuel ration sensor 2 of the first embodiment. The liner air-fuel ration sensor 2 comprises a cylindrical main body metal 38 in which a screw portion 39 for fixing the air-fuel ration sensor 2 to an exhaust pipe is formed on an external surface thereof, a sheet-like gas sensing device 4 extending in an axial direction (length direction of the liner air-fuel ration sensor 2: vertical direction in the Figure), a cylindrical ceramic sleeve 6 disposed so as to surround the periphery in the diameter direction of the gas sensing device 4, an insulating contact member 66 disposed such that the inner wall face of a contact through hole 68 passing therethrough in the axial direction surrounds the periphery of the rear end portion of the gas sensing device 4 and five connecting terminals 10 (two pieces indicated in FIG. 1) disposed between the gas sensing device 4 and the insulating contact member 66.

The main body metal 38 is so constructed in substantially cylindrical shape having a through hole 54 which goes through in the axial direction and a shelf portion 52 projecting inward in the diameter direction of the through hole 54. In the main body metal 38, the front end side (detecting portion 8 described later) of the gas sensing device 4 is disposed outside of the front end side of the through hole 54 while electrode terminal portions 120, 121 are disposed outside of the rear end side of the through hole 54, and passed through the through hole 54 and held. The shelf portion 52 is formed as a tapered face directed inward having an inclination with respect to a plane perpendicular to the axial direction.

An annular ceramic holder 51, powder charging layers 53, 56 (hereinafter, called talc rings 53, 56 depending on a case) and the aforementioned ceramic sleeve 6 are overlaid in this order from a front end side to a rear end side inside the through hole 54 in the main body metal 38, surrounding the periphery of the diameter direction of the gas sensing device 4. A caulking packing 57 is disposed between the ceramic sleeve 6 and the rear end portion 40 of the main body metal 38 and a metal holder 58 which holds the talc ring 53 and the ceramic holder 51 so as to maintain air tightness is disposed between the ceramic holder 51 and the shelf portion 52 of the main body metal 38. The rear end portion 40 of the main body metal 38 is caulked so as to press the ceramic sleeve 6 to the side of the front end through the caulking packing 57.

On the other hand, as shown in FIG. 1, metal double structured protectors (for example, made of stainless steel) having a plurality of holes, comprising an outside protector 42 and an inside protector 43 are attached to the outer periphery on the front end side (down in FIG. 1) of the main body metal 38 so as to cover the projecting portion of the gas sensing device 4 by welding or the like.

An outer cylinder 44 is fixed to the outer periphery on the rear end side of the main body metal 38. A grommet 50 including lead wire passing holes 61 in which five lead wires 46 (only three are expressed in FIG. 1) are passed through, those lead wires being electrically connected to the electrode terminal portions 120, 121 of the gas sensing device 4 is disposed at an opening portion on the rear end side (up in FIG. 1) of the outer cylinder 44.

The insulating contact member 66 is disposed on the rear end side (up in FIG. 1) of the gas sensing device 4 projecting from the rear end portion 40 of the main body metal 38. This insulating contact member 66 is disposed around the electrode terminal portions 120, 121 formed on the surface on the rear end side of the gas sensing device 4. The insulating contact member 66 is formed into a cylindrical configuration having a contact through hole 68 which goes through in the axial direction and has a projecting portion 67 projecting outward in the diameter direction from an external surface thereof. The insulating contact member 66 is disposed within the outer cylinder 44 such that the projecting portion 67 makes contact with the outer cylinder 44 via a holding member 69.

Next, the gas sensing device 4 which is a major portion of the present invention will be described.

The gas sensing device 4 is formed into a sheet-like shape extending in the axial direction and a detecting portion 8 is formed on the front end side (down in the figure) which is directed to gas as a measuring object. The electrode terminal portions 120, 121 are formed on the front and rear surfaces of an outer surface on the rear end side (up in the figure). In the meantime, the porous portion 30 (see FIGS. 1, 4) is formed in the detecting portion 8. The connecting terminal 10 is disposed between the gas sensing device 4 and the insulating contact member 66 so that it is electrically connected to the electrode terminal portions 120, 121 of the gas sensing device 4. The connecting terminal 10 is also connected electrically to the lead wire 46 introduced from outside and disposed inside the sensor so as to form a current passage for current flows between an external device which the lead wire is connected to and the electrode terminal portions 120, 121.

Figure 2:
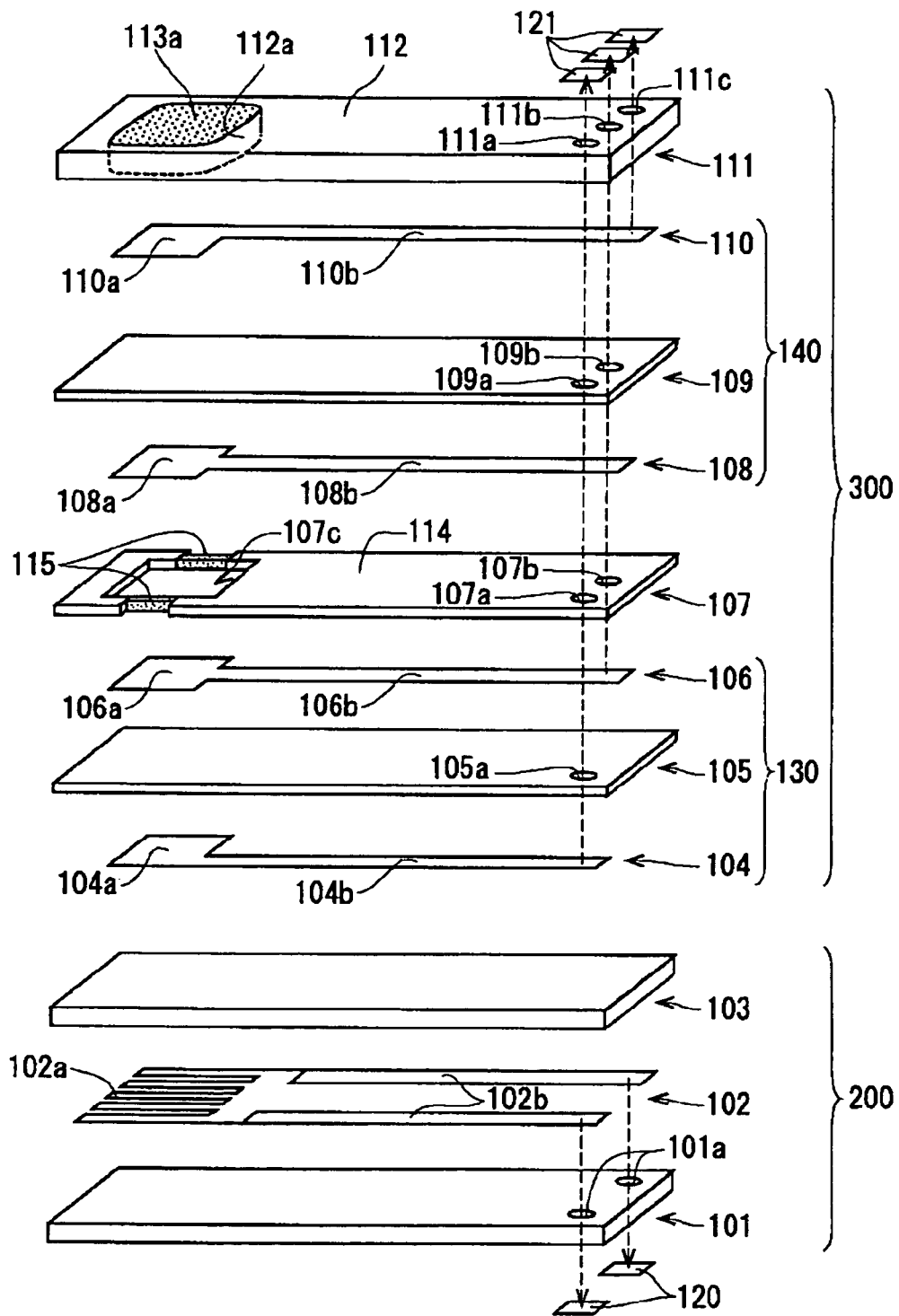
FIG. 2 is an exploded view of a sensing device 4 disposed in the gas sensor 2 of the first embodiment.
Figure 3:
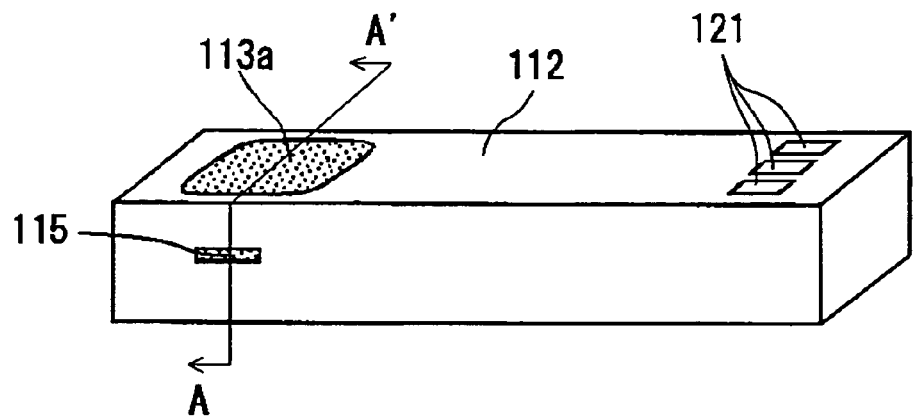
FIG. 3 is a perspective view of the gas sensor 2 of the first embodiment.
Figure 4:
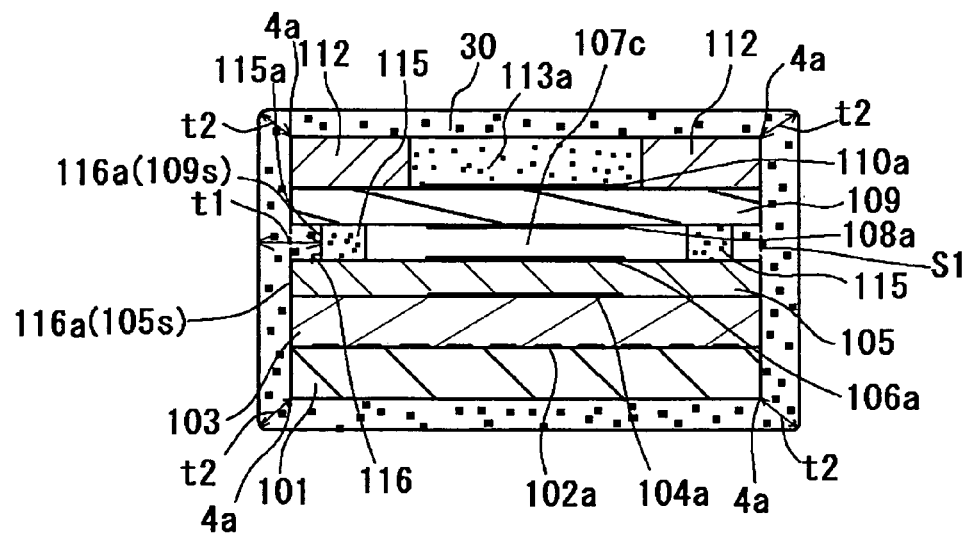
FIG. 4 is a sectional view taken along the line A-A' of FIG. 3.

Next, the gas sensing device 4 will be described specifically with reference to FIGS. 2-4. FIG. 2 is an exploded view of the lamination of the gas sensing device 4, FIG. 3 is a perspective view of the gas sensing device and FIG. 4 is a sectional view taken along the line A-A' of FIG. 3. The porous portion 30 is not indicated in FIGS. 2, 3 for the reason of the description below.

As shown in FIG. 2, the gas sensing device 4 is comprised of a lamination of a detecting device 300 and a heater 200 and the detecting device 300 is comprised of a lamination of an oxygen concentration detecting cell 130 and an oxygen pump cell 140.

The heater 200 comprises a first base body 101 and a second base body 103 composed of mainly alumina and a heating body 102 composed of mainly platinum and sandwiched between the first base body 101 and the second base body 103. The heating body 102 comprises a heating portion 102a located at the front end side and a pair of heater lead portions 102b extending in the length direction of the first base body 101 from the heating portion 102a. Then, the terminals of the heater lead portions 102b are connected electrically to electrode terminal portions 120 through heater side through holes 101a provided in the first base body 101.

The oxygen concentration detecting cell 130 comprises a first solid electrolyte body 105 and first electrode 104 and second electrode 106 formed on both faces of the first solid electrolyte body 105. The first electrode 104 is comprised of a first electrode portion 104a and a first lead portion 104b extending in the length direction of the first solid electrolyte body 105 from the first electrode portion 104a. The second electrode 106 is comprised of a second electrode portion 106a and a second lead portion 106b extending in the length direction of the first solid electrolyte body 105 from the second electrode portion 106a.

The terminal of the first lead portion 104b is connected electrically to the electrode terminal portion 121 through a first through hole 105a provided in the first solid electrolyte body 105, a second through hole 107a provided in an insulating layer 107 described later, a fourth through hole 109a provided in a second solid electrolyte body 109 and a sixth through hole 111a provided in protective layer 111. On the other hand, the terminal of the second lead portion 106b is connected electrically to an electrode terminal portion 121 through a third through hole 107b provided in an insulating layer 107 described later, a fifth through hole 109b provided in the second solid electrolyte body 109 and a seventh through hole 111b provided in the protective layer 111.

On the other hand, an oxygen pump cell 140 comprises a second solid electrolyte body 109 and third electrode 108 and fourth electrode 110 formed on both faces of the second solid electrolyte body 109. The third electrode 108 is comprised of a third electrode portion 108a and a third lead portion 108b extending in the length direction of the second solid electrolyte body 109 from the third electrode portion 108a. The fourth electrode 110 is comprised of a fourth electrode portion 110a and a fourth lead portion 110b extending in the length direction of the second solid electrolyte body 109 from the fourth electrode portion 110a.

The terminal of the third lead portion 108b is connected electrically to the electrode terminal portion 121 through the fifth through hole 109b provided in the second solid electrolyte body 109 and the seventh through hole 111b provided in the protective layer 111. On the other hand, the terminal of the fourth lead portion 110b is connected electrically to the electrode terminal portion 121 through an eighth through hole 111c provided in the protective layer 111 described later. In the meantime, the second lead portion 106b and the third lead portion 108b are in the same potential through the third through hole 107b.

The first solid electrolyte body 105 and the second solid electrolyte body 109 are constituted of partially stabilized zirconia sintered body produced by adding yttria ($Y_2O_3$) or calcia (CaO) to zirconia ($ZrO_2$) as stabilizer.

The heating element 102, first electrode 104, second electrode 106, third electrode 108, fourth electrode 110, electrode terminal portion 120 and electrode terminal portion 121 may be formed of platinum group element. As the platinum group element preferable for forming these, Pt, Rh, Pd and the like can be mentioned. One of them may be used independently or two or more may be used at the same time.

More preferably, the heating element 102, first electrode 104, second electrode 106, third electrode 108, fourth electrode 110, electrode terminal portion 120 and electrode terminal portion 121 are formed of mainly Pt if considering heat resistance and oxidation resistance. It is more preferable that the heating body 102, first electrode 104, second electrode 106, third electrode 108, fourth electrode 110, electrode terminal portion 120 and electrode terminal portion 121 contain ceramic component as well as platinum group element which is a main component. This ceramic component is preferred to be of the same component as main material (for example, component mainly constituting the first solid electrolyte body 105 and the second solid electrolyte body 109) of a side on which each element is overlaid from viewpoints of fixing.

The insulating layer 107 is formed between the oxygen pump cell 140 and the oxygen concentration detecting cell 130. The insulating layer 107 is comprised of an insulating portion 114 and a diffusion rate controlling portion 115. A gas detecting chamber 107c is formed at a position corresponding to the second electrode portion 106a and the third electrode portion 108a in the insulating portion 114 of this insulating layer 107. This gas detecting portion 107c communicates with outside in the width direction of the insulating layer 107 and a diffusion rate controlling portions 115 which achieve gas diffusion between outside and the gas detecting chamber 107c under a predetermined rate controlling condition are disposed in the communicating portions.

The insulating portion 114 is not restricted to any particular one as long as it is a ceramic sintered body having insulation property and oxide base ceramics such as alumina, mullite or the like can be picked up.

The diffusion rate controlling portion 115 is a porous body composed of alumina. This diffusion rate controlling portion 115 controls the diffusion rate when a detecting objects gas flows into the gas detecting chamber 107c.

The protective layer 111 is formed on the surface of the second solid electrolyte body 109 so as to sandwich the fourth electrode 110. In this protective layer 111, porous electrode protecting portion 113a which sandwiches the fourth electrode portion 110a is inserted into a through hole 112a formed in a reinforcing portion 112 which sandwiches the fourth lead portion 110b.

As shown in FIG. 4, in the diffusion rate controlling portion 115, its external face 115a directed to an outermost virtual face S1 which connects the outermost faces of the gas sensing device 4 is located inside the outermost virtual face S1. The outermost virtual face S1 is formed of the external faces of the first base body 101, second base body 103, first solid electrolyte body 105, second solid electrolyte 109, reinforcing portion 112 and electrode protecting portion 113a in the first embodiment and indicated with a solid line or dotted line in FIG. 4. Then, a concave portion 116 is formed such that it is dented from the outer most virtual face S1 toward the external face 115a of the diffusion rate controlling portion 115.

The porous portion 30 is formed on an opposite side to the gas detecting chamber 107c via the diffusion rate controlling portion 115. More specifically, the porous portion 30 covers the periphery of the outermost virtual face S1 of the gas sensor device 4 while part thereof invades into the concave portion 116.

Because the porous portion 30 is disposed at least such that it makes contact with an opening periphery 116a (in the first embodiment, an external face 105s of the first solid electrolyte body 105, an external face 109s of the second solid electrolyte body 109, an external face 107s (not shown) of the insulating body 107) of the concave portion 116, the opening edge of the concave portion 116 can be blocked from being exposed to the outermost virtual face S1, so that gas can be blocked from invading into the diffusion rate controlling portion 115 through this opening edge from outside. Thus, generation of clogging in the diffusion rate controlling portion 115 can be suppressed to improve the accuracy of detection of air-fuel ratio by changes in diffusion resistance of a measuring object gas.

Further, part of the porous portion 30 invades into the concave portion 116. Because part of the porous portion 30 invades into the concave portion 116 so as to form a wedge-like configuration, the porous portion 30 can be prevented from separating from the gas sensing device 4 as compared to a case where a porous portion is disposed to be in contact with only the opening edge 116a of the concave portion 116 in the gas sensing device 4.

Further, by allowing part of the porous portion 30 to invade into the concave portion 116 in the gas sensing device 4, the thickness of the porous portion 30 (minimum thickness t1 described later) of the porous portion 30 can be secured without enlarging the gas sensing device 4 and consequently, the porous portion 30 can absorb phosphorous and silicone more without delaying the activation time of the gas sensing device 4.

This porous portion 30 has a smaller diffusion resistance than the diffusion rate controlling portion 115 and the minimum thickness t1 between the external face of the porous portion 30 provided in the concave portion 116 and the internal face directed to the diffusion rate controlling portion 115 is 150 µm. By setting the thickness of the porous portion 30 larger than 130 µm, a distance over which a measuring object gas passes through the porous portion 30 can be increased, so that the porous portion 30 can absorb phosphorous and silicone more. Accordingly, generation of clogging in the diffusion rate controlling portion 115 can be suppressed to improve the accuracy of detection of air-fuel ratio by changes of the diffusion resistance of the measuring object gas.

The BET specific surface area of the porous portion 30 is 1.6 m$^2$/g. Because the BET specific surface area of the porous portion 30 is set to more than 1.0 m$^2$/g, the diameter of particles forming the porous portion 30 is smaller so that the porous portion 30 can absorb more phosphorous and silicone. Consequently, generation of clogging in the diffusion rate controlling portion 115 can be suppressed so as to improve the accuracy of detection of air-fuel ratio by changes in diffusion resistance of a measuring object gas.

Further, the porous portion 30 covers a corner portion 4a extending in the length direction of the detecting portion 8 of the gas sensing device 4 and the thickness t2 of the porous portion 30 from this corner portion 4a is 70 µm. By covering the corner portion 4a in the length direction of the gas sensing device 4 with the porous substance based on the fact that the porous portion 30 is composed of the porous substance, water droplets adhering to the porous portion 30 can be diffused until they reach the corner portion 4a of the gas sensing device 4 because they penetrate slowly while being diffused into a number of pores. As a result, a thermal shock generated on the corner portion 4a of the gas sensing device 4 can be suppressed thereby preventing crack from being generated in the gas sensing device 4.

In the meantime, the oxygen concentration detecting cell 130 of the first embodiment corresponds to "a first cell" in the scope of claim of patent, the first solid electrolyte body 105 corresponds to "a first solid electrolyte layer", the first electrode 104 and the second electrode 106 correspond to "a first opposing electrode", the oxygen pump cell 140 corresponds to "a second cell", the second solid electrolyte body 109 corresponds to "a second solid electrolyte layer", the third electrode 108 and fourth electrode 110 correspond to a second opposing electrode, the diffusion rate controlling portion 115 corresponds to "a first porous portion", the insulating portion 114 corresponds to "an insulating body" and the porous portion 30 corresponds to "a second porous portion".

Next, the manufacturing method of this gas sensing device 4 will be described.

A portion before sintering and a portion after sintering will be explained with the same reference numeral. For example, the first solid electrolyte body after sintering and the non-sintered first solid electrolyte body will be explained with same reference numeral 105.

First, slurry in which a first raw material powder and a plasticizer were dispersed by wet blending was prepared. The first raw material powder is composed of, for example, alumina powder 97 mass % and silica 3 mass % as sintering adjusting agent. The plasticizer is composed of butyral resin and dibutylphthalate (DBP). After this slurry was formed into a sheet-like matter of 0.4 mm thick according to a sheet forming method using a doctor blade apparatus, this was cut to 140 mm×140 mm so as to obtain the non-sintered reinforcing portion 112, first non-sintered base body 101, second non-sintered base body 103 and the non-sintered insulating portion 114 of the non-sintered insulating layer 107. Then, the through hole 112a was formed in the non-sintered reinforcing portion 112. Additionally, the gas detecting chamber 107 was formed in the non-sintered insulating portion 114.

On the other hand, slurry in which the second raw material powder and plasticizer were dispersed by wet blending was prepared. The second raw material powder is composed of, for example, alumina powder 63 mass %, silica 3 mass % as sintering adjusting agent and carbon power 34 mass %. The plasticizer is composed of butyral resin and DBP. Then, the non-sintered electrode protecting portion 113a was obtained by using this slurry.

Further, slurry in which the third raw material powder and plasticizer were dispersed by wet blending was prepared. The third raw material powder is composed of, for example, zirconia powder 97 mass %, 3 mass % of silica ($SiO_2$) powder and alumina powder as sintering adjusting agent. The plasticizer is composed of butyral resin and DBP. The first solid electrolyte body 105 and the second solid electrolyte body 109 were obtained using this slurry.

Further, slurry in which alumina powder 100 mass % and plasticizer were dispersed by wet blending was prepared. The plasticizer is composed of butyral resin and DBP. The non-sintered diffusion rate controlling portion 115 of the non-sintered insulating layer 107 was obtained using this slurry.

Then, the first non-sintered base body 101, non-sintered heating element 102, second non-sintered base body 103, first non-sintered electrode 104, first non-sintered solid electrolyte body 105, second non-sintered electrode 106, non-sintered insulating layer 107, third non-sintered electrode 108, second non-sintered solid electrolyte body 109, fourth non-sintered electrode 110, non-sintered protective layer 111 and the like are overlaid successively from the bottom.

More specifically, the non-sintered heating element 102 is formed on the first non-sintered base body 101 by screen printing using paste mainly composed of platinum. Then, The second non-sintered base body 103 is overlaid so as to sandwich the non-sintered heating element 102.

Then, the first non-sintered electrode 104 was formed on the first non-sintered solid electrolyte body 105. The first non-sintered electrode 104 is composed of platinum paste constituted of platinum 90 mass % and zirconia power 10 mass %. The first non-sintered electrode 104 is formed according to screen printing method using this platinum paste.

The first non-sintered electrode 104 was overlaid on the second non-sintered base body 103 and the second non-sintered electrode 106 was formed on the first non-sintered solid electrolyte body 105 by printing. In the meantime, the second non-sintered electrode 106 is made of the same material as the first non-sintered electrode 104.

Then, the non-sintered insulating layer 107 was formed on the second non-sintered electrode 106. More specifically, the non-sintered insulating portion 114 and the non-sintered diffusion rate controlling portion 115 were formed. Paste mainly composed of carbon was printed at a portion which turns to the gas detecting chamber 107c after sintering.

The third non-sintered electrode 108 was printed on the second non-sintered solid electrolyte body 109 and the second non-sintered solid electrolyte body 109 was overlaid on the non-sintered insulating layer 107 in such a manner to sandwich the third non-sintered electrode 108. Then, the fourth non-sintered electrode 110 was printed on the second non-sintered solid electrolyte body 109. The third non-sintered electrode 108 and the fourth non-sintered electrode 110 are made of the same material as the first non-sintered electrode 104. Then, the non-sintered protective layer 111 was overlaid on the fourth non-sintered electrode 110. In the non-sintered protective layer 111, the non-sintered electrode protecting portion 113a is already inserted into the through hole 112a in the non-sintered reinforcing portion 112.

These components were pressed at 1 MPa and then cut to a predetermined size, so that 10 pieces of non-sintered laminations were obtained from a single formation.

After that, resin was diffused by heating from the non-sintered gas sensing device and it was held at a sintering temperature of 1500° C. for an hour and consequently, a lamination for detecting the concentration of oxygen in exhaust gas was sintered.

Through the sintering process, the first non-sintered electrode 104 turns to the first electrode 104 comprising the first electrode portion 104a and the first lead portion 104b. The first non-sintered solid electrolyte body 105 turns to the first solid electrolyte body 105. The second non-sintered electrode 106 turns to the second electrode 106 comprising the second electrode portion 106a and the second lead portion 106b. The non-sintered insulating portion 114 of the non-sintered insulating layer 107 turns to the insulating portion 114 and the non-sintered diffusion rate controlling portion 115 of the non-sintered insulating layer 107 turns to the porous diffusion rate controlling portion 115. The non-sintered insulating layer 107 turns to the insulating layer 107. The gas detecting chamber 107c in the insulating layer 107 communicates with outside through the diffusion rate controlling portions 115 on both sides in the width direction of the insulating portion 114. The diffusion rate controlling portion 115 realizes gas diffusion between outside and the gas detecting chamber 107c under a predetermined diffusion rate controlling condition. The third non-sintered electrode 108 turns to the third electrode 108 comprising the third electrode portion 108a and the third lead portion 108b. The second non-sintered solid electrolyte body 109 turns to the second solid electrolyte body 109. The fourth non-sintered electrode 110 turns to the fourth electrode 110 comprising the fourth electrode portion 110a and the fourth lead portion 110b. The non-sintered reinforcing portion 112 of the non-sintered protective layer 111 turns to the reinforcing portion 112 for protecting the second solid electrolyte body 109 and the non-sintered electrode protecting portion 113a of the non-sintered protective layer 111 turns to the porous electrode protecting portion 113a for controlling the fourth electrode 110 from poisoning.

After that, the non-sintered porous portion 30 is formed around the front end side of this lamination. More specifically, slurry was produced of spinel powder, titania and a remnant was produced of alumina sol, and the non-sintered porous portion 30 was formed on the entire periphery on the front end side of the lamination using this slurry. In the meantime, as its formation method, spray, coating and the like may be used. After that, by treating the lamination having this formed non-sintered porous portion 30 with heat for three hours in sintering time under a sintering temperature of 1000° C., the gas sensing device 4 including the porous portion 30 was obtained.

The gas sensing device 4 produced in the above manufacturing method is inserted into the metal holder 58 and fixed with the ceramic holder 51 and talc ring 53 so as to produce an assembly. After that, this assembly is fixed to the main body metal 38 and the talc ring 56 and the separator 6 were inserted. The rear end side 40 of the main body metal 38 was caulked so as to produce a lower assembly. The outside protector 42 and the inside protector 43 are already installed to the lower assembly. On the other hand, an upper assembly is produced by installing the outer cylinder 44, insulating contact member 66 and grommet 50 and the like. Then, the lower assembly and the upper assembly are jointed to obtain the gas sensor 2.

Hereinafter a gas sensor 202 according to the second embodiment of the present invention will be described with reference to the accompanying drawings. In the meantime, the gas sensor 202 of the second embodiment is different from the gas sensor 2 of the first embodiment in the structure of the gas sensing device 204 and thus, mainly the gas sensing device 204 will be described while description of other components is simplified or omitted.

Figure 5:
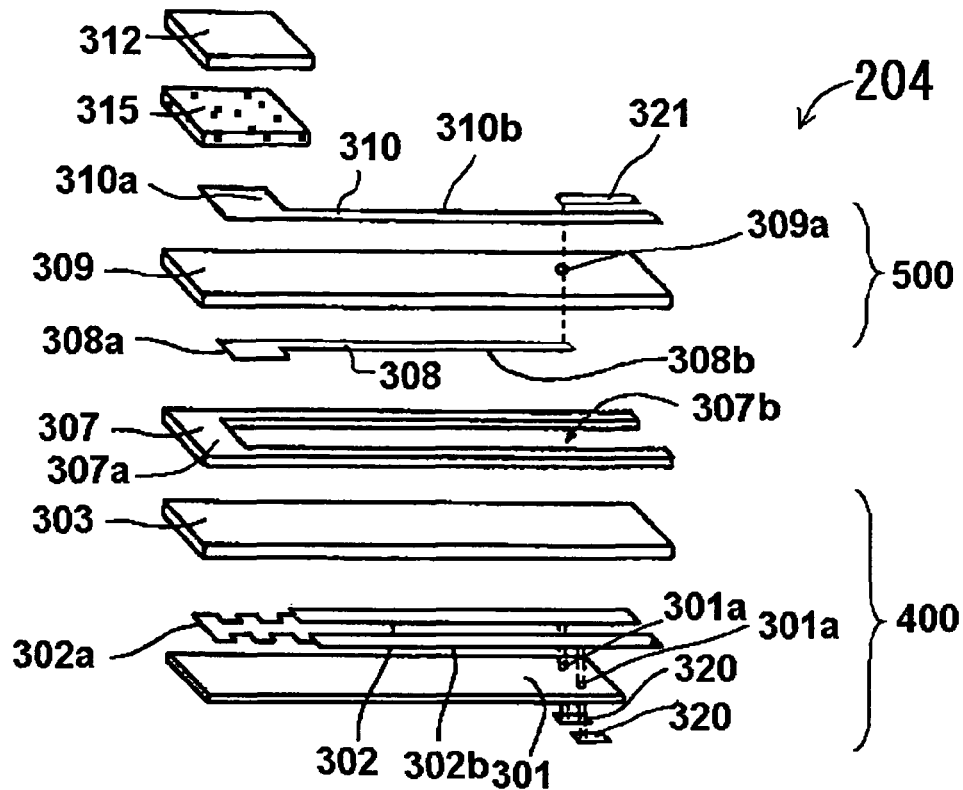
FIG. 5 is an exploded view of a sensing device 204 disposed in a gas sensor 202 of the second embodiment.
Figure 6:
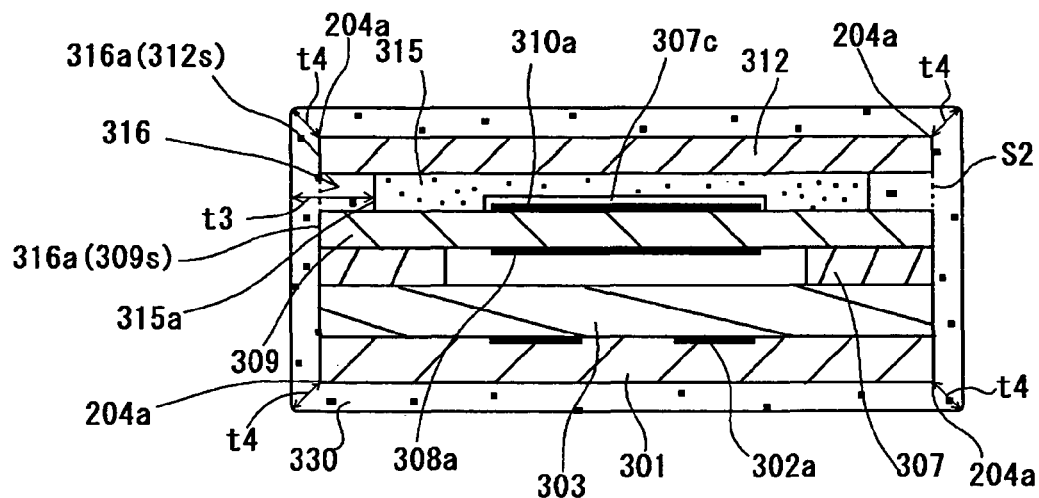
FIG. 6 is a sectional view of a device in the vicinity of a detecting portion of FIG. 5.

FIG. 5 is an exploded view of the lamination of the gas sensing device 204 and FIG. 6 is a sectional view of the detecting portion of FIG. 5. FIG. 5 does not show the porous portion 30 for the reason of the description below.

In the gas sensing device 204, as shown in FIG. 5, an oxygen pump cell 500 and a heater 400 are overlaid.

The heater 400 comprises a first base body 301 and second base body 303, both composed of mainly alumina and a heating element 302 composed of mainly platinum and sandwiched between the first base body 301 and the second base body 303. The heating element 302 is comprised of a heating portion 302a located on the front end side and a pair of heater lead portions 302b extending in the length direction of the first base body 301 from the heating portion 302a. The terminal of the heater lead portion 302b is connected electrically to an electrode terminal portion 320 through a heater side through hole 301a provided in the first base body 301.

The oxygen pump cell 500 comprises a first solid electrolyte body 309 and a first electrode 308 and second electrode 310 formed on both faces of the first solid electrolyte body 309. The first electrode 308 is comprised of a first electrode portion 308a and a first lead portion 308b extending in the length direction of the first solid electrolyte body 309 from the first electrode portion 308a. The second electrode 310 is comprised of a second electrode portion 310a and a second lead portion 310b extending in the length direction of the first solid electrolyte body 309 from the second electrode portion 310a. Then, the terminal of the first lead portion 308b is connected electrically to an electrode terminal portion 321 through a first through hole 309a provided in the first solid electrolyte body 309.

The second solid electrolyte body 309 is constituted of partially stabilized zirconia sintered body composed by adding yttria ($Y_2O_3$) or calcia (CaO) as stabilizer to zirconia ($ZrO_2$).

The heating element 302, first electrode 308, second electrode 310, electrode terminal portion 320 and electrode terminal portion 321 can be formed of platinum group element. As preferable platinum group element for forming these, Pt, Rh, Pd and the like can be picked up. One of those may be used independently or two or more may be used at the same time.

The insulating layer 307 is formed between the heater 400 and the oxygen pump cell 500. The insulating layer 307 is comprised of an insulating portion 307a and an atmosphere introduction port 307b. This atmosphere introduction port 307b communicates with outside on the rear end side of the insulating layer 307. The insulating portion 307b is not restricted to any particular one as long as it is a ceramic sintered body having insulation property and for example, oxide base ceramics such as alumina, mullite or the like can be mentioned.

A gas measuring chamber 307c (see FIG. 6) is provided on the surface of the first solid electrolyte body 309 such that it surrounds the second electrode portion 310a of the second electrode 310 and the gas measuring chamber 307c is covered with the first porous portion 315. Further, a shielding layer 312 is overlaid on an opposite side to the first solid electrolyte body 309 of the first porous portion 315. The first porous portion 315 is a porous body composed of alumina.

As shown in FIG. 6, in the first porous portion 315, its external surface 315a facing the outermost virtual face S2 connecting the outermost faces of the gas sensing device 204 is located inside the outermost virtual face S2. In the meantime, according to the second embodiment, the outermost virtual face S2 is formed of the external surfaces of the first base body 301, second base body 303, insulating layer 307, first solid electrolyte body 309 and shielding layer 312, referring to a face indicated with a solid line and dotted line in FIG. 6. Then, a concave portion 316 is formed such that it is dented from the outermost virtual face S2 toward the external surface 315a of the first porous portion 315.

Further, a second porous portion 330 is formed outside the first porous portion 315. More specifically, the second porous portion 330 covers the periphery of the outermost virtual face S2 of the gas sensing device 204 while part of them invades into the concave portion 316.

By disposing the second porous portion 330 such that it makes at least contact with an opening edge 316a (in the second embodiment, external face 309s of the first solid electrolyte body 309 and external face 312s of the shielding body 312), the opening edge of the concave portion 316 can be prevented from being exposed to the outermost virtual face S2 of the gas sensing device 204 thereby blocking gas from invading into the first porous portion 315 through this opening edge. Thus, generation of clogging in the first porous portion 315 can be suppressed.

Further, part of this second porous portion 330 invades into the concave portion 316. Because part of the second porous portion 330 invades into the concave portion 316 so as to form a wedge-like configuration, the second porous portion 330 can be prevented from being separated from the gas sensing device 204 as compared to a case where a second porous portion is disposed to make contact with only the opening edge 316a of the concave portion 316 in the gas sensing device 204.

Further, by allowing part of the second porous portion 330 to invade into the concave portion 316 in the gas sensing device 204, the thickness (minimum thickness t3 described later) of the second porous portion 330 can be secured without enlarging the gas sensing device 204. As a consequence, the second porous portion 330 can absorb phosphorus and silicone without delaying the activation time of the gas sensing device 204.

The minimum thickness t3 between the external face of the porous portion 330 provided in the concave portion 316 and the internal face facing the first porous portion 315 is 150 µm. By setting the minimum thickness t3 of the second porous portion 330 to larger than 130 µm, the distance over which a measuring object gas passes through the second porous portion 330 can be increased so that more phosphorous and silicone can be absorbed by the second porous portion 330.

The BET specific surface area of the second porous portion 330 is 1.6 $m^2$/g. Because the BET specific surface area of the second porous portion 330 is set to more than 1.0 $m^2$/g, the diameter of particles forming the porous portion 330 is smaller so that the porous portion 330 can absorb more phosphorous and silicone.

Further, the porous portion 330 covers a corner portion 204a extending in the length direction of the detecting portion 208 of the gas sensing device 204 and the thickness t4 of the second porous portion 330 from this corner portion 204a is 70 µm. Based on the fact that the second porous portion 330 is composed of the porous substance, by covering the corner portion 204a in the length direction of the gas sensing device 204 with the porous substance, water droplets adhering to the second porous portion 330 can be diffused until they reach the corner portion 204a of the gas sensing device 204 because they penetrate slowly while being diffused into a number of pores. As a result, thermal shock generated on the corner portion 204a of the gas sensing device 204 can be suppressed thereby preventing crack from being generated in the gas sensing device 204.

The oxygen pump cell 500 of the second embodiment corresponds to "a first cell" in the scope of claim for patent, the first solid electrolyte body 309 corresponds to "a first solid electrolyte layer" and the first electrode 308 and second electrode 310 correspond to "a first opposing electrode".

Hereinafter, a gas sensor 600 according to the third embodiment of the present invention will be described with reference to the accompanying drawings. The gas sensor 600 of the third embodiment is different from the first gas sensor 2 only in the structures of the gas sensing device 204 and gas sensing device 804 and mainly the gas sensing device 804 will be described while description of other components is simplified or omitted.

Figure 7:
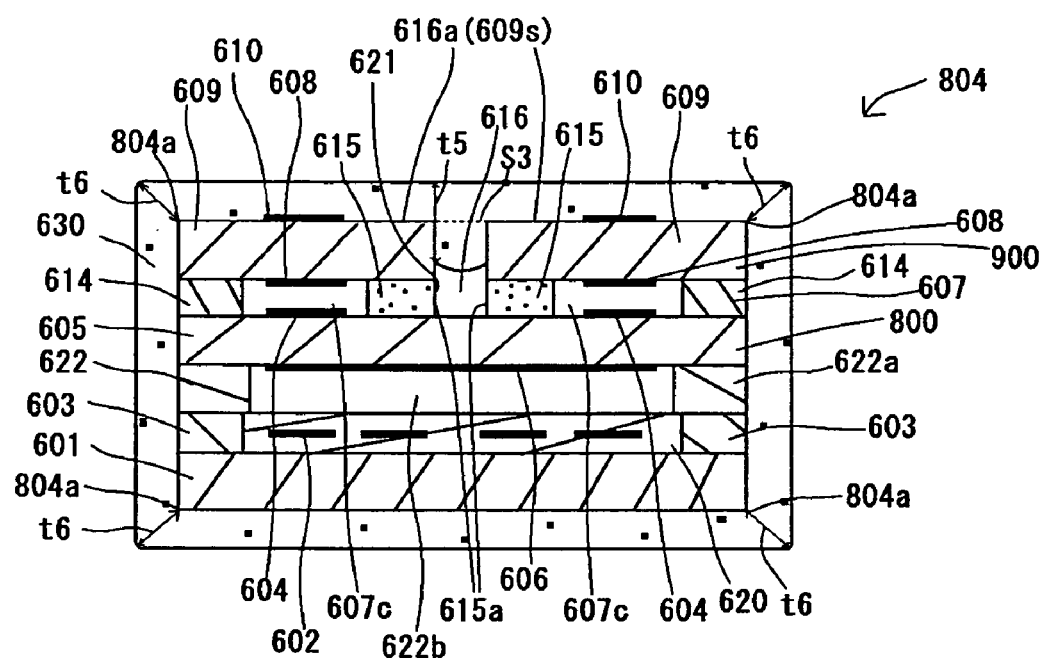
FIG. 7 is a sectional view of a sensing device 804 disposed in a gas sensor 600 of the third embodiment.

FIG. 7 is a sectional view of the detecting portion 608 in the gas sensing device 804. As shown in FIG. 7, the gas sensing device 804 comprises a first base body 601 and a second base body 603 formed on the first base body 601 such that it contains cavity internally. Then, a third base body 620 is disposed in the cavity and the third base body 620 contains a heating element 602 composed of mainly platinum.

An oxygen concentration detecting cell 800 is comprised of a first solid electrolyte body 605 and a first electrode 604 and second electrode 606 formed on both faces of the first solid electrolyte 605. On the other hand, an oxygen pump 900 is comprised of a second solid electrolyte 609 and a third electrode 608 and fourth electrode 610 formed on both faces of the second solid electrolyte 609. A through hole 621 is formed in the second solid electrolyte body 609 such that it goes through in the lamination direction.

An insulating layer 607 is formed between the oxygen pump cell 900 and the oxygen concentration detecting cell 800. The insulating layer 607 is comprised of an insulating portion 614 and a diffusion rate controlling portion 615. A gas detecting chamber 607c is formed at a position corresponding to the first electrode 604 and third electrode 608 in the insulating portion 614 of the insulating layer 607. This gas detecting chamber 607c communicates with outside through the through hole 621 provided in the second solid electrolyte body 609 and a diffusion rate controlling portion 615 for achieving gas diffusion between outside and the gas detecting chamber 607c under a predetermined diffusion rate controlling condition is disposed in this communicating portion.

An interposing layer 622 is formed between the second base body 602 and the third base body 603 and the oxygen concentration detecting cell 800. This interposing layer 622 is comprised of an interposing portion 622a and an atmosphere introduction port 622b. This atmosphere introduction port 622b communicates with outside on the rear end side of the gas sensing device 804.

The first solid electrolyte body 605, second solid electrolyte body 609, first base body 601, second base body 603, insulating portion 614, and interposing layer 622 are constituted of partially stabilized zirconia sintered body produced by adding yttria ($Y_2O_3$) or calcia (CaO) to zirconia ($ZrO_2$) as stabilizer.

The heating element 602, first electrode 604, second electrode 606, third electrode 608, and fourth electrode 610 may be formed of platinum group element. As the platinum group element preferable for forming these, Pt, Rh, Pd and the like can be mentioned. One of them may be used independently or two or more may be used at the same time.

The third base body 620 is not restricted to any particular one as long as it is a ceramic sintered body having insulation property and for example, oxide base ceramics such as alumina, mullite or the like may be picked up. The diffusion rate controlling portion 615 is a porous body composed of alumina. A diffusion rate when the detection gas flows out to the gas detecting chamber 607c is controlled by the diffusion rate controlling portion 615.

In the diffusion rate controlling portion 615, an external surface 615a directed to the outermost virtual face S3 connecting the outermost faces of the gas sensing device 804 is located inside the outermost virtual face S3. In the meantime, the outermost virtual face S3 mentioned in the third embodiment is composed of the external surfaces of the first base body 601, second base body 603, interposing portion 622a, first solid electrolyte body 605, insulating portion 614, second solid electrolyte body 609 and fourth electrode 610 and indicated with a solid line or dotted line in FIG. 7. Then, a concave portion 616 is formed such that it is dented from the outermost virtual face S3 toward the external surface 615a of the diffusion rate controlling portion 615.

Further, a porous portion 630 is formed on an opposite side to the gas detecting chamber 607c via the diffusion rate controlling portion 615. More specifically, the porous portion 630 covers the periphery of the outermost virtual face S3 of the gas sensing device 804 while part thereof invades into the concave portion 616.

By disposing the porous portion 630 at least in contact with the opening edge 616a (in the third embodiment, an external face 609s of the second solid electrolyte body 609) of the concave portion 616, the opening edge of the concave portion 616 can be prevented from being exposed to the outermost virtual face S3 of the gas sensing device 804, thereby blocking gas from invading into the diffusion rate controlling portion 615 through this opening edge. Thus, generation of clogging in the diffusion rate controlling portion 615 can be suppressed to improve the accuracy of detection of air-fuel ratio by changes in diffusion resistance of the measuring object gas.

Further, part of this porous portion 630 invades into the concave portion 616. Because part of the porous portion 630 invades into the concave portion 616 so as to form a wedge-like configuration, the porous portion 630 can be prevented from being separated from the gas sensing device 804 as compared to a case where a porous portion 630 is disposed to make contact with only the opening edge 616a of the concave portion 616 in the gas sensing device 804.

Further, by allowing part of the porous portion 630 to invade into the concave portion 616 in the gas sensing device 804, the thickness (minimum thickness t5 described later) of the porous portion 630 can be secured without enlarging the gas sensing device 804. As a consequence, the porous portion 630 can absorb phosphorus and silicone without delaying the activation time of the gas sensing device 804.

The porous portion 630 has a smaller diffusion resistance than the diffusion rate controlling portion 615 and the minimum thickness t5 between the external face of the porous portion 630 provided in the concave portion 616 and the internal face directed to the diffusion rate controlling portion 615 is 150 μm. By setting the minimum thickness t5 of the porous portion 630 to larger than 130 μm, the distance over which a measuring object gas passes through the porous portion 330 can be increased so that more phosphorous and silicone can be absorbed by the porous portion 630. Thus, generation of clogging in the diffusion rate controlling portion 615 can be suppressed to improve the accuracy of detection of air-fuel ratio by changes in diffusion resistance of the measuring object gas.

Further, the BET specific surface area of the porous portion 630 is 1.6 $m^2$/g. Because the BET specific surface area of the porous portion 630 is set to more than 1.0 $m^2$/g, the diameter of particles forming the porous portion 630 is smaller so that the porous portion 630 can absorb more phosphorous and silicone. Thus, generation of clogging in the diffusion rate controlling portion 615 can be suppressed to improve the accuracy of detection of air-fuel ratio by changes in diffusion resistance of the measuring object gas.

Further, the porous portion 630 covers a corner portion 804a extending in the length direction of the detecting portion 608 of the gas sensing device 804 and the thickness t6 of the porous portion 630 from this corner portion 804a is 70 μm. Based on the fact that the porous portion 630 is composed of the porous substance, by covering the corner portion 804a in the length direction of the gas sensing device 804 with the porous substance, water droplets adhering to the porous portion 630 can be diffused until they reach the corner portion 804a of the gas sensing device 804 because they penetrate slowly while being diffused into a number of pores. As a result, thermal shock generated on the corner portion 804a of the gas sensing device 804 can be suppressed thereby preventing crack from being generated in the gas sensing device 804.

The oxygen concentration detecting cell 800 of the third embodiment corresponds to "the first cell" in the scope of claim of patent, the first solid electrolyte body 605 corresponds to "the first solid electrolyte layer", the first electrode 604 and second electrode 606 correspond to "the first opposing electrode", the oxygen pump 900 corresponds to "the second cell", the second solid electrolyte body 609 corresponds to "the second solid electrolyte layer", the third electrode 608 and fourth electrode 610 correspond to the second opposing electrode, the diffusion rate controlling portion 615 corresponds to "the first porous portion", the insulating portion 614 corresponds to "the insulating body" and the porous portion 630 corresponds to "the second porous portion".

Embodiment

Next, the effect of the present invention was confirmed in the gas sensing device 4 of the first embodiment.

First, a lamination was produced in the above-described method. The non-sintered porous portion 30 was formed in this lamination such that the minimum thickness t1 between the external face of the porous portion 30 and the internal face directed to the diffusion rate controlling portion 115 was 60 μm, 130 μm, 200 μm and 300 μm. By treating the lamination in which the non-sintered porous portion 30 was formed with heat, the gas sensing device 4 was produced. Then, each gas sensing device 4 was installed to the main body metal 38 and outer cylinder 44 and the like so as to produce the gas sensor 2.

Figure 8:
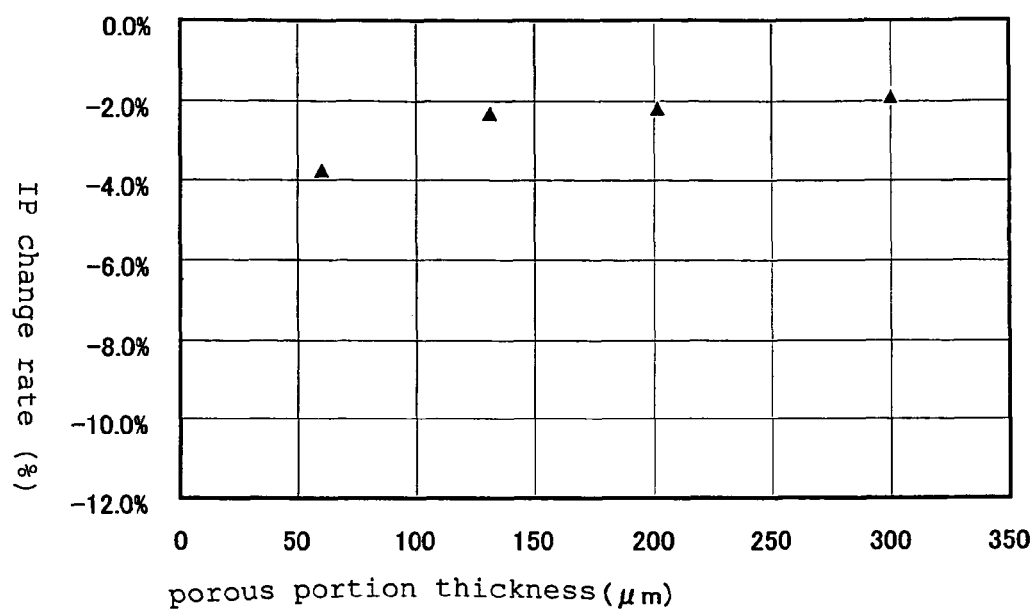
FIG. 8 is a graph showing a result of poisoning durability test depending on the thickness of a porous portion 30.

Poisoning durability test was performed to each gas sensor 2. In this poisoning durability test, a 1.6-liter inline four-cylinder engine was used and a gas sensor 2 was exposed under a condition of engine revolution number of 3000 rpm (air oil ratio λ=1), exhaust gas temperature of 500° C., P poisoning component (ZnDTP: 1.3 cc/L, calcium sulfonate: 1.0 cc/L), and device temperature of 830° C. and it was picked up after 60 hours so as to measure IP value. FIG. 8 shows its result.

The gas sensor 2 in which the thickness t1 of the porous portion 30 is 60 μm has an IP change rate of −4.0% from FIG. 8. Contrary to this, it is evident that the gas sensor 2 in which the thickness t1 of the porous portion 30 is 130 μm, 200 μm, 300 μm has an excellent detection accuracy of air-fuel ratio because its IP change rate is near −2.0%. That is, it is evident that the gas sensor of the embodiment can absorb much phosphorous and silicone through the porous portion 30 thereby suppressing generation of clogging in the diffusion rate controlling portion 115.

The embodiments of the present invention has been described and the present invention is not restricted to the above-described embodiments but may be modified and improved in various ways within a range in which the present invention can be achieved.

For example, although according to this embodiment, the diffusion rate controlling portion 115 and the first porous portion 315 are in contact with the porous portion 30 and the second porous portion 330, this embodiment is not restricted to this example, but the diffusion rate controlling portion 115 and the first porous portion 315 may be separated from the porous portion 30 and the second porous portion 330.

Although according to this embodiment, the porous portions 30, 530 and the second porous portion 330 cover the entire periphery of the gas sensor devices 4, 204, 804, this embodiment is not restricted to this example, but they may cover the opening edge of the concave portions 116, 316, 616.

Although according to the first embodiment and second embodiment, two concave portions 116, 316 are formed in the width direction of the gas sensor device 4, 204, it is permissible to form any one of them. In the second embodiment, a concave portion 316 may be provided on the front end side or rear end side of the gas sensing device 4.

What is claimed is:

1. A sheet-like gas sensing device, comprising:
   a first cell having a first solid electrolyte layer and first opposing electrodes formed on the front and rear faces of the first solid electrolyte layer;
   a first porous portion overlaid on said first cell,
   a hollow measuring chamber defined only by said first cell and said first porous portion, wherein gas is introduced into said hollow measuring chamber through said first porous portion, said hollow chamber communicating with one of the first opposing electrodes;
   a shielding layer overlaid on said first porous portion;
   part of an external face of said first porous portion directed toward an outermost virtual face (S1, S2, S3) defined by an outermost side face of the gas sensing device, said external face of the first porous portion being located inside the outermost virtual face of the sensing device so that the part of said first porous portion is recessed from the outermost virtual face of the sensing device thereby forming a recessed cavity that includes the external face of said first porous portion, and
   a second porous portion having a smaller diffusion resistance than the first porous portion, a portion of said second porous portion extending into the recessed cavity and a portion of said second porous portion being disposed on said outermost side face of said gas sensing device overlaying at least an opening edge of the recessed cavity.

2. The gas sensing device according to claim 1, further comprising:
   a second cell having a second solid electrolyte layer and second opposing electrodes formed on the front and rear faces of the second solid electrolyte layer, said second cell overlaid on the first cell with one of the second opposing electrodes facing the measuring chamber, and
   an insulating layer formed between the first cell and the second cell, the insulating layer forming the measuring chamber together with the first cell, the second cell and the first porous portion.

3. The gas sensing device according to claim 2 wherein, the minimum thickness (t1, t5) of the second porous portion within the recessed cavity and measured from the external face of the second porous portion to an internal face of the second porous portion that is directed toward the first porous portion, is more than 130 μm.

4. The gas sensing device according to claim 2 or 3 wherein the measuring chamber and the first porous portion are provided on the front end side of the gas sensing device, and the second porous portion at least covers one or more of corner portions extending in the length direction on the front end side of the gas sensing device and the thickness (t2, t6) of the second porous portion is more than 20 μm from the corner portion.

5. The gas sensing device according to claim 1, wherein the minimum thickness (t3) of the second porous portion provided in the recessed cavity from the external face thereof to the internal face directed to the first porous portion is more than 130 μm.

6. The gas sensing device according to claim 1 or 5 wherein,
   the measuring chamber and the first porous portion are provided on the front end side of the gas sensing device and,
   the second porous portion at least covers one or more of corner portions extending in the length direction on the front end side of the gas sensing device and the thickness (t4) of the second porous portion is more than 20 μm from the corner portion.

7. A gas sensor according to claim 1, 2, 3 or 5, further comprising:
   a cylindrical main body metal holding said gas sensing device.

* * * * *